United States Patent [19]

Hubele

[11] Patent Number: 4,940,806
[45] Date of Patent: Jul. 10, 1990

[54] MICROBICIDES

[75] Inventor: Adolf Hubele, Magden, Switzerland

[73] Assignee: Ciba-Geigy Corporation, Ardsley, N.Y.

[21] Appl. No.: 369,563

[22] Filed: Jun. 21, 1989

Related U.S. Application Data

[62] Division of Ser. No. 931,289, Nov. 17, 1986, Pat. No. 4,853,399.

[30] Foreign Application Priority Data

Nov. 22, 1985 [CH] Switzerland ............... 4985/85

[51] Int. Cl.$^5$ ............... C07D 319/06; C07D 319/08; C07D 317/16
[52] U.S. Cl. ............... 549/365; 549/374; 549/375; 549/445; 549/447; 549/453; 549/454
[58] Field of Search ............ 549/365, 374, 445, 453, 549/454, 447, 375

[56] References Cited

U.S. PATENT DOCUMENTS 4,160,838  7/1979  Reet et al. ............... 71/76
4,602,010  7/1986  Heeres et al. ............ 514/184
4,810,718  3/1989  Colle et al. ............. 514/383

*Primary Examiner*—Nicky Chan
*Attorney, Agent, or Firm*—George R. Dohmann; Edward McC. Robets

[57] ABSTRACT

Novel substituted 2-(1H-1,2,4-triazolyl)-1-phenylethan-1-one ketals of the general formula

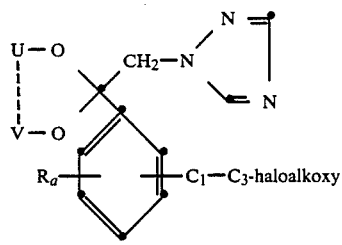

wherein one of the two phenyl substituents is in 2-position and the other is in 4-position, and wherein $R_a$ is halogen, methyl or $C_1$-$C_3$haloalkoxy, and U and V are each independently of the other $C_1$-$C_{12}$alkyl, unsubstituted or substituted by halogen or $C_1$-$C_6$alkoxy, or together are an alkylene bridge selected from

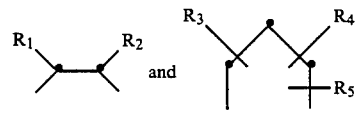

wherein $R_1$ to $R_5$ are as defined herein, and the acid addition salts and metal complex salts, have microbicidal properties and are especially suitable for controlling phytopathogenic microorganisms. They can be used in the form of plant protective or seed dressing agents for preventing or controlling plant pathogens.

1 Claim, No Drawings

MICROBICIDES

This is a divisional of application Ser. No. 931,289, filed on Nov. 17, 1986, now U.S. Pat. No. 4,853,399.

The present invention relates to novel haloalkoxy-substituted 2-(1H-1,2,4-triazolyl)-1-phenylethan-1-one ketals of formula I below and to the acid addition salts and metal complexes thereof. The invention further relates to the preparation of these compounds and to microbicidal compositions which contain, as at least one active component, a compound of formula I. The invention also relates to the preparation of said compositions and to the use of the compounds of formula I and the compositions containing them for controlling harmful microorganisms.

Specifically, the invention relates to compounds of formula I

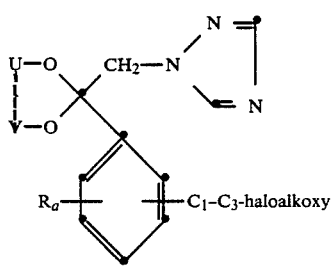

(I)

wherein one of the two phenyl substituents is in 2-position and the other is in 4-position, and wherein $R_a$ is halogen, methyl or $C_1$–$C_3$ haloalkoxy, U and V are each independently of the other $C_1$–$C_{12}$ alkyl, unsubstituted or substituted by halogen or $C_1$–$C_6$ alkoxy, or both taken together are an alkylene bridge selected from

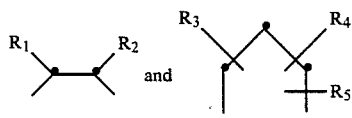

wherein $R_1$ and $R_2$ are each independently of the other hydrogen, $C_1$–$C_6$ alkyl, $C_1$–$C_6$ alkyl which is substituted by one or more halogen atoms, or are phenyl or phenyl which is substituted by one or more halogen atoms and/or $C_1$–$C_2$ alkyl groups or are the group —CH$_2$—Z—R$_6$; or $R_1$ and $R_2$ together form a tetramethylene bridge which is unsubstituted or substituted by $C_1$–$C_4$ alkyl; and Z is an oxygen or sulfur atom, $R_6$ is hydrogen, $C_1$–$C_6$ alkyl or $C_1$–$C_6$ alkyl which is substituted by one or more halogen atoms or $C_1$–$C_3$ alkoxy groups, or is $C_3$–$C_4$ alkenyl, 2-propynyl (=propargyl), 3-halo-2-propynyl, or is phenyl or benzyl, each unsubstituted or substituted in the aromatic ring by one or more of halogen $C_1$–$C_3$ alkyl, $C_1$–$C_3$ alkoxy, nitro and/or CF$_3$;

$R_3$, $R_4$ and $R_5$ are each independently hydrogen or $C_1$–$C_4$ alkyl, with the proviso that the total number of carbon atoms in $R_3$, $R_4$ and $R_5$ may not exceed 6;

and to the acid addition salts and metal complex salts thereof.

Depending on the indicated number of carbon atoms, alkyl by itself or as moiety of another substituent will be understood as meaning for example the following groups: methyl, ethyl, propyl, butyl, pentyl, hexyl, heptyl, octyl, nonyl, decyl, undecyl or dodecyl, and the isomers thereof, e.g. isopropyl, isobutyl, tert-butyl, sec-butyl, isopentyl and the like. Alkenyl may be 1-propenyl, allyl, 1-butenyl, 2-butenyl or 3-butenyl. Throughout this specification, halogen, halo and Hal shall be understood as meaning fluorine, chlorine, bromine or iodine, with fluorine, chlorine or bromine being preferred.

Depending on the indicated number of carbon atoms, haloalkoxy is a straight chain mono- or perhalogenated O-alkyl group containing identical or different halogen atoms. Examples of such halogenated groups are: —OCH$_2$F, —OCHF$_2$, —OCF$_3$, —OCH$_2$Cl, —OCCl$_3$, —OCHFCl, —OCClF$_2$, —OCF$_2$CHF$_2$, —OCF$_2$CFCl$_2$, —OCF$_2$CHFCl, —OCF$_2$CF$_2$Cl, —OCF$_2$CCl$_3$, —OCF$_2$CHCl$_2$, —OCF$_2$CH$_3$, —OCH$_2$CF$_3$, OCH$_2$CH$_2$Cl, —OCH$_2$CH$_2$F, —OCH$_2$CF$_2$Br, —OCClFCFCl$_2$, —OCHFCF$_2$Br, and —OCF$_2$CHFCF$_3$.

The invention relates to the free compounds of the formula I as well as to the acid addition salts thereof with inorganic and organic acids, and likewise to their complexes with metal salts.

Salts of this invention are in particular addition salts with inorganic or organic acids which are physiologically tolerable with respect to the envisage utility.

Examples of inorganic and organic acids which are physiologically tolerable with respect to the utility as microbicides in plant protection, are hydrohalic acids, e.g. hydrochloric, hydrobromic or hydriodic acid, sulfuric acid, phosphoric acid, phosphorous acid, nitric acid, unsubstituted or halogenated fatty acids such as acetic acid, trichloroacetic acid and oxalic acid, or sulfonic acids such as benzenesulfonic acid and methanesulfonic acid.

Metal complex salts of formula I consist of the basic organic molecule and an inorganic or organic metal salt, e.g. the halides, nitrates, sulfates, phosphates, tartrates etc. of copper, manganese, iron, zinc and other metals. The metal cations may exist in different valence states.

The compounds of formula I are oils, resins or solids which are stable at room temperature and which possess very valuable physiological properties, such as microbicidal, especially phytofungicidal properties. They may therefore be used in agriculture or related fields for controlling phytopathogenic microorganisms. Compared with the closest structurally related compounds of the prior art, the compounds of this invention which are haloalkoxylated in the phenyl nucleus have a significantly enhanced microbicidal activity and good biodegradability, so that their use is safe in regard to environmental pollution.

On account of their pronounced microbicidal activity, preferred compounds of formula I are those containing the following substituents or combinations thereof.

Preferred compounds of formula I are those wherein the $C_1$–$C_3$ haloalkoxy substituent contains at least one or more identical or different halogen atoms selected from the group consisting of fluorine, chlorine and bromine and, irrespective of the possibilities afforded by the number of carbon atoms, contains 0–4 hydrogen atoms, $R_a$ is fluorine, chlorine, bromine, methyl or any $C_1$–$C_3$ haloalkoxy group as defined above;

U and V are each independently of the other $C_1$–$C_6$ alkyl or together form an alkylene bridge as defined in formula I, wherein $R_1$ is hydrogen or $C_1$–$C_2$ alkyl, and $R_2$ is $C_1$–$C_6$ alkyl or $C_1$–$C_6$ alkyl which is substituted by one or more halogen atoms, or is phenyl or phenyl which is substituted by 1 to 3 halogen atoms and/or $C_1$–$C_2$ alkyl groups, or is the group —$CH_2$—O—$R_6$, wherein $R_6$ is hydrogen, $C_1$–$C_6$ alkyl, $C_1$–$C_3$ alkyl which is substituted by one or more halogen atoms or $C_1$–$C_3$ alkoxy groups, or is $C_3$–$C_4$ alkenyl or propargyl, or phenyl or benzyl, each unsubstituted or substituted in the aromatic ring by 1 to 3 identical or different members selected from halogen, $C_1$–$C_2$ alkyl, $C_1$–$C_2$ alkoxy, nitro and/or $CF_3$; and wherein $R_1$ and $R_2$, when taken together, are able to form an unsubstituted or methyl-substituted tetramethylene bridge; and wherein $R_3$, $R_4$ and $R_5$ are each independently hydrogen or alkyl groups of not more than 4 carbon atoms (group Ia).

Within the above group Ia, those compounds of formula I are preferred in which the $C_1$–$C_3$ haloalkoxy group has a meaning selected from:

| | | |
|---|---|---|
| (A) —$OCHF_2$ | (H) —$OCF_2$—$CHFBr$ | (O) —$OCBr_3$ |
| (B) —$OCF_2$—$CHF_2$ | (I) —$OCH_2$—$CF_3$ | (P) —$OCF_2Br$ |
| (C) —$OCF_2$—$CFCl_2$ | (J) —$OCH_2$—$CH_2Cl$ | (Q) —$OC_2F_5$ |
| (D) —$OCF_2$—$CHCl_2$ | (K) —$OCH_2$—$CH_2F$ | (R) —$OCF_3$ |
| (E) —$OCF_2$—$CHFCl$ | (L) —$OCH_2$—$CCl_3$ | (S) —$OCH_2Cl$ |
| (F) —$OCF_2$—$CCl_3$ | (M) —$OCF_2$—$CHF$—$CF_3$ | (T) —$OCHFCl$ |
| (G) —$OCF_2$—$CFCl_2$ | (N) —$OCCl_3$ | (U) —$OCH_2Br$; |

$R_a$ is fluorine, chlorine, bromine, methyl or any $C_1$–$C_3$ haloalkoxy group as defined in (A) to (U);

U and V are each independently of the other $C_1$–$C_6$ alkyl or together form an alkylene bridge as defined in formula I, wherein $R_1$ is hydrogen or $C_1$–$C_2$ alkyl, and $R_2$ is $C_1$–$C_6$ alkyl or $C_1$–$C_3$ alkyl which is substituted by one or more fluorine or chlorine atoms, or is phenyl or phenyl which is substituted by 1 or 2 halogen atoms and/or methyl groups, or is the group —$CH_2$—O—$R_6$, wherein $R_6$ is $C_1$–$C_6$ alkyl, $C_1$–$C_3$ alkyl which is substituted by one or more fluorine and/or chlorine atoms or also by $C_1$–$C_3$ alkoxy groups, or is $C_3$–$C_4$ alkenyl, propargyl, or phenyl or benzyl, each unsubstituted or substituted in the aromatic ring by 1 or 2 identical or different members selected from fluorine, chlorine, bromine, methyl, methoxy nitro and/or $CF_3$; and wherein $R_1$ and $R_2$, when taken together, are able to form an unsubstituted or methyl-substituted tetramethylene bridge; and wherein $R_3$ is hydrogen and $R_4$ and $R_5$ are each independently of the other hydrogen, methyl, ethyl or n-propyl, but together contain from 0 to 4 carbon atoms (group Ib).

Within the group Ib, those compounds of formula I are preferred in which the $C_1$–$C_3$ haloalkoxy group has a meaning selected from:

| | |
|---|---|
| (A) —$OCHF_2$ | (F) —$OCF_2$—$CCl_3$ |
| (B) —$OCF_2$—$CHF_2$ | (G) —$OCF_2$—$CFCl_2$ |
| (C) —$OCF_2$—$CFCl_2$ | (H) —$OCF_2$—$CHFBr$ |
| (D) —$OCF_2$—$CHCl_2$ | (I) —$OCH_2$—$CF_3$ |
| (E) —$OCF_2$—$CHFCl$ | (M) —$OCF_2$—$CHF$—$CF_3$; |

$R_a$ is fluorine, chlorine, bromine, methyl or any $C_1$–$C_3$ haloalkoxy group as defined in (A) to (I) or (M);

U and V are each independently of the other $C_1$–$C_6$ alkyl or together form an alkylene bridge as defined in formula I, wherein $R_1$ is hydrogen or $C_1$–$C_2$ alkyl, and $R_2$ is $C_1$–$C_4$ alkyl or $C_1$–$C_2$ alkyl which is substituted by one or more fluorine or chlorine atoms, or is phenyl or phenyl which is substituted by 1 or 2 chlorine atoms and/or methyl groups, or is the group —$CH_2$—O—$R_6$, wherein $R_6$ is $C_1$–$C_4$ alkyl, $C_1$–$C_3$ alkyl which is substituted by 1 to 3 fluorine atoms or methoxy groups, or is $C_3$–$C_4$ alkenyl or propargyl, or phenyl or benzyl, each unsubstituted or substituted in the aromatic ring by 1 or 2 members selected from fluorine, chlorine, methyl, methoxy, nitro and/or $CF_3$; and wherein $R_1$ and $R_2$, when taken together, are able to form an unsubstituted or methyl-substituted tetramethylene bridge; and wherein $R_3$ is hydrogen, $R_4$ is hydrogen, methyl or ethyl, $R_5$ is hydrogen, methyl, ethyl or n-propyl, and $R_3$, $R_4$ and $R_5$ together contain from 0 to 4 carbon atoms (group Ic).

Within group Ic above, those compounds of formula I are preferred in which the $C_1$–$C_3$ haloalkoxy group has a meaning selected from:

| | |
|---|---|
| (A) —$OCHF_2$ | (E) —$OCF_2CHFCl$ |
| (B) —$OCF_2$—$CHF_2$ | (G) —$OCF_2CFCl_2$. |

$R_a$ is fluorine, chlorine, bromine, methyl or any $C_1$–$C_2$ haloalkoxy 3roup as defined in (A), (B), (E) or (G)

U and V are each independently of the other $C_1$–$C_6$ alkyl or together form an alkylene bridge as defined in formula I, wherein $R_1$ is hydrogen or $C_1$–$C_2$ alkyl, and $R_2$ is hydrogen, $C_1$–$C_4$ alkyl, $C_1$–$C_2$ alkyl which is substituted by one or more fluorine or chlorine atoms, or is phenyl or phenyl which is substituted by a chlorine atom and/or a methyl group, or is the group —$CH_2$—O—$R_6$, wherein $R_6$ is $C_1$–$C_4$ alkyl, $C_1$–$C_3$ alkyl which is substituted by 1 to 3 fluorine atoms or methoxy groups, or is $C_3$–$C_4$ alkenyl or propargyl, or phenyl, or phenyl which is substituted by a member selected from fluorine, chlorine, methyl and/or $CF_3$; and wherein $R_3$ is hydrogen, $R_4$ is hydrogen, methyl or ethyl, $R_5$ is hydrogen, methyl or ethyl, and $R_3$, $R_4$ and $R_5$ together contain from 0 to 4 carbon atoms (group Id).

Within the group Id above, those compounds of formula I are preferred in which the haloalkoxy group has a meaning selected from:

| | |
|---|---|
| (A) —$OCHF_2$ | (E) —$OCF_2CHFCl$ |
| (B) —$OCF_2CHF_2$ | (G) —$OCF_2CFCl_2$ |

$R_a$ is fluorine, chlorine, bromine, methyl, $OCHF_2$ or $-OCF_2CHF_2$;

U and V are each independently of the other $C_1-C_6$ alkyl or together form an alkylene bridge as defined in formula I, wherein $R_1$ is hydrogen or methyl, and $R_2$ is hydrogen, $C_1-C_3$ alkyl, $C_1-C_2$ alkyl which is substituted by one or more fluorine or chlorine atoms, or is phenyl which is substituted by a chlorine atom, or is the group $-CH_2-O-R_6$, wherein $R_6$ is $C_1-C_3$ alkyl, $C_1-C_2$ alkyl which is substituted by 1 to 3 fluorine atoms, or is $C_3-C_4$ alkenyl or propargyl, or phenyl; and wherein $R_3$ is hydrogen, $R_4$ is hydrogen, methyl or ethyl, $R_5$ is hydrogen or methyl; and $R_3$, $R_4$ and $R_5$ together contain from 0 to 2 carbon atoms (group Ie).

The compounds of formula I are prepared by (A) condensing a triazole of formula II

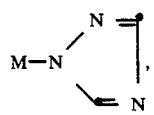   (II)

wherein M is hydrogen or a metal cation, with a compound of formula III

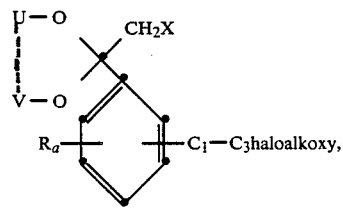   (III)

wherein X is a nucleophilic leaving group, or (B) in a compound of formula IV

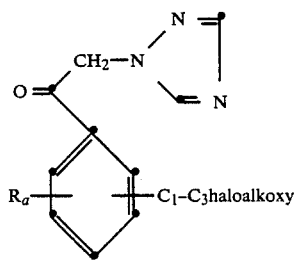   (IV)

converting the carbonyl function into a ketal function of formula

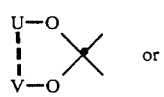   (V)

(C) to prepare compounds of formula I, wherein U and V together are a group of formula $-CH_2-CH(CH_2ZR_6')-$ and $R_6'$ is radical $R_6$ which differs from hydrogen, condensing a compound of formula VI with a compound of formula VII

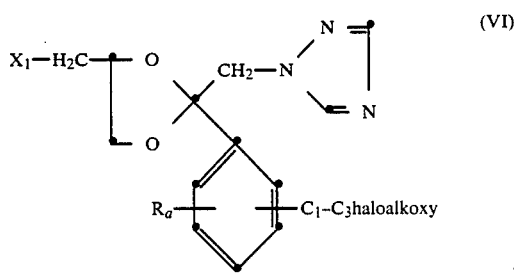   (VI)

and

   (VII)

wherein one of $X_1$ and $X_2$ is a hydroxy or mercapto group which may be in salt form, e.g. of formula $-Z-M$, and the other is any nucleophilic leaving group X, or $X_1$ as well as $X_2$ are hydroxy groups, or (D) hydrolysing hydrazines of formula IX

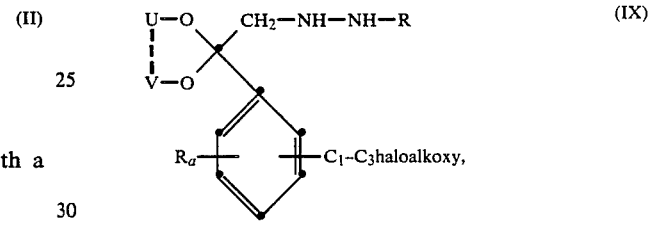   (IX)

(a) wherein R is $-CHO$, $-COR'$, $-COOR'$ or $-CONH_2$, and R' is $C_1-C_4$ alkyl, benzyl or phenyl, and converting the resultant compound of formula IX, in which R is hydrogen, or a salt thereof with an inorganic or organic acid, with the aid of formamide and/or [3-(dimethylamino)-2-azaprop-2-en-1-ylidene]-dimethylammonium chloride (aza salt), $[(CH_3)_2N^+=CH-N=CH-N(CH_3)_2]Cl^-)$, into a compound of formula I; or (b) converting compounds of formula IX, wherein R is $-COR'$, into the N,N'-bisformyl derivatives with aqueous formic acid and cyclising said derivatives with formamide, in the absence or presence of $NH_3$ or an $NH_3$ donor, to a triazole derivative of formula I, where R in formula IX is hydrogen, $-CHO$, $-COR'$, $-COOR'$ or $-CONH_2$ and R' is $C_1-C_4$ alkyl, benzyl or phenyl, and if desired, converting a resultant compound into another compound of formula I and/or a resultant free compound into an acid addition salt, or converting an acid addition salt into the free compound or into another acid addition salt, or converting a resultant free compound or acid addition salt into a metal complex, and the substituents in the above formulae are as defined for formula I.

Examples of metal cations M are alkali metal cations, e.g. lithium, sodium or potassium cations, or alkaline earth metal cations, e.g. magnesium, calcium, strontium or barium cations.

The nucelophilic leaving groups referred to above are e.g. reactive esterified hydroxyl groups such as hydroxyl groups which are esterified with a hydrohalic acid, e.g. with hydrofluoric, hydrochloric, hydrobromic or hydriodic acid, or with a lower alkanesulfonic acid, and unsubstituted or substituted benzenesulfonic or a halosulfonic acid, e.g. with methanesulfonic acid, ethanesulfonic acid, benzenesulfonic acid, p-toluenesulfonic acid or fluorosulfonic acid.

Variant A: The reaction of a triazole of formula II

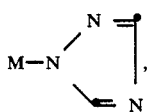  (II)

wherein Me is preferably a metal atom, especially an alkali metal atom, with a compound of formula III

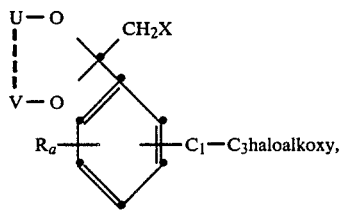  (III)

wherein $R_a$, U and V are as defined for formula I and X is a leaving group, e.g. halogen, preferably chlorine, bromine or iodine, or benzenesulfonyloxy, p-tosyloxy, trifluoroacetyloxy or, preferably, lower alkylsulfonyloxy, e.g. mesyloxy, is preferably conducted in a relatively polar but inert organic solvent, e.g. N,N-dimethylformamide, hexamethylphosphoric triamide (HMPT), N,N-dimethylacetamide, dimethylsulfoxide, acetonitrile, benzonitrile and the like. Such solvents may be employed in combination with other inert solvents such as aliphatic or aromatic hydrocarbons, e.g. benzene, toluene, xylene, hexane, petroleum ether, chlorobenzene, nitrobenzene and the like.

If X is chlorine or bromine, an alkali metal iodide (such as NaI or KI) may conveniently be added to speed up the reaction. Elevated temperatures in the range from 0° to 220° C., preferably from 80° to 170° C., are advantageous. It is convenient to heat the reaction mixture under reflux.

Where M in formula II is hydrogen, the process is carried out in the presence of a base. Examples of suitable bases are inorganic bases such as the oxides, hydroxides, hydrides, carbonates and bicarbonates of alkali metals and alkaline earth metals, as well as organic bases e.g. tertiary amines such as triethylamine, triethylenediamine, piperidine, pyridine, 4-dimethylaminopyridine, 4-pyrrolidylpyridine and the like.

In this process variant, and in the subsequent ones, the intermediates and final products may be isolated from the reaction medium and, if desired, purified by one of the methods conventionally employed, e.g. by extraction, crystallisation, chromatography, distillation and the like.

Variant B: The conversion of the carbonyl group in compounds of formula IV into the group of formula V is carried out by reaction with an orthocarboxylic acid $C_1$-$C_{12}$ trialkyl ester, the $C_1$-$C_{12}$ alkyl groups of which may be substituted by halogen or $C_1$-$C_6$ alkoxy, or in the presence of an acid, with at least 2 moles of a monohydric alcohol of the formula U—OH (Va), to give compounds of formula I in which U and V are identical unsubstituted or substituted $C_1$-$C_{12}$ alkyl groups, or by reaction with a diol of the formula Vb

 (Vb)

to give compounds of the formula I, wherein U and V together are one of the alkylene bridges defined at the outset. In the foregoing, Y, $R_a$, U and V are as defined for formula I.

This ketalisation reaction may be carried out in similar manner to already known ketalisation reactions, e.g. in similar manner to the preparation of 2-bromomethyl-2,4-diphenyl-1,3-dioxolane [Synthesis, 1974 (I), 23].

In the preferred embodiment of the ketalisation, both reactants are heated for several hours under reflux together with an entrainer in a conventional organic solvent. Examples of suitable entrainers are benzene, toluene, xylene, chloroform or carbon tetrachloride. To hasten the reaction it may be convenient to add a strong acid, e.g. p-toluenesulfonic acid. Examples of suitable organic solvents are in this case aromatic hydrocarbons such as benzene, toluene, xylene and the like, saturated hydrocarbons such as n-hexane, or saturated halogenated hydrocarbons such as 1,1,1-trichloroethane.

The ketalisation may also be carried out by other methods, e.g. by reacting a ketone (IV) which has been ketalised with an alcohol or phenol which differs from the alkanol or diol of the formula Va or Vb respectively, and effecting transketalisation with an excess of alkanol Va or diol Vb to a compound (I). The starting material may be obtained e.g. by process variant (A).

Variant C: Compounds of formula I, wherein U and V in variant (C) are together —$CH_2$—$CH(CH_2ZR_6')$—, are obtained e.g. by reaction of a compound of formula VI with a compound of formula VII, wherein $X_1$ is a —OH or —SH group and $X_2$ is a nucleophilic leaving group X. The reaction is preferably carried out in an inert organic solvent. Examples of suitable solvents for this reaction are N,N-dimethylformamide, N,N-dimethylacetamide, hexamethylphosphoric triamide, dimethylsulfoxide, 4-methyl-3-pentanone and the like. Mixtures with other inert solvents, e.g. with aromatic hydrocarbons such as benzene, toluene, xylene and others, may also be used. In some cases it may be convenient to carry out the reaction in the presence of a base to speed up the reaction rate. Examples of suitable bases are alkali metal hydrides or alkali metal carbonates. It may also be advantageous in certain cases to convert the compound of the formula VI first into a suitable metal salt. This is preferably accomplished by reaction of VI with a sodium compound, e.g. sodium hydride, sodium hydroxide and the like. This salt of the compound of formula VI is subsequently reacted with the compound of formula VII. To increase the reaction rate, the process may also be carried out in some cases at elevated temperature, preferably in the range from 80° to 130° C. or at the boiling point of the solvent.

Compounds of the formulae VI and VII, wherein $X_1$ is a leaving group X and $X_2$ is a —OH or —SH group, may also be reacted in similar manner.

In the condensation reaction of compounds of formulae VI and VII, wherein $X_1$ and $X_2$ are hydroxy, to give compounds of formula I wherein Z is oxygen, the reactants may be heated in a suitable solvent under reflux, while simultaneously distilling off water from the reaction mixture as an azeotrope. Suitable solvents are aromatic hydrocarbons such as toluene or the alcohol HO—$R_6$ itself. This reaction is conveniently carried out in a strong acid, e.g. p-toluenesulfonic acid.

Variant D: Hydrazines of formula IX, wherein R is not hydrogen, are hydrolysed, before the cyclisation, in a manner known per se and in the presence of an acid or a base, to compounds of formula IX, wherein R is hydrogen, or salts thereof. Examples of eligible bases are hydroxides or carbonates of alkali metals and alkaline earth metals such as sodium hydroxide, potassium hydroxide and calcium hydroxide, or corresponding carbonates. It is preferred to carry out the hydrolysis in the presence of a strong acid, preferably an inorganic acid such as HCl, sulfuric acid or phosphoric acid. The hydrolysis can be carried out in aqueous or aqueous-organic medium such as a water/alkanol mixture, especially in a mixture of water and methanol or ethanol.

For the cyclisation of process variant (a), the formamide and/or the [3-(dimethylamino)-2-azaprop-2-en-1-ylidene]-dimethylammonium chloride are conveniently employed in not less than equimolar amount, based on the compound of formula IX (R=H). The reaction is preferably carried out in the presence of an inert organic solvent, e.g. an alkanol, ester, ether or amide of the kind mentioned above, a $C_2$–$C_5$ alkylnitrile such as acetonitrile, propionitrile, butyronitrile, and also benzonitrile, a 3-alkoxypropionitrile containing 1 or 2 carbon atoms in the alkoxy moiety, e.g. 3-methoxypropionitrile and 3-ethoxypropionitrile. A preferred solvent for the reaction with the aza salt is a $C_1$–$C_5$ alkanol, most preferably ethanol. It is preferred to use excess formamide as solvent for the reaction with formamide. The reaction temperature for the cyclisation of process variant (a) is in general in the range from 20° to 200° C., preferably from 20° to 180° C.

For the formylation of compounds of formula IX, wherein R is COR', e.g. —$COCH_3$, —$COC_2H_5$ or —$COC_3H_7$, according to process variant (b), it is convenient to use 85% aqueous formic acid. The reaction temperature is preferably in the range from 70° to 100° C. The formamide is preferably employed in not less than equimolar amount, based on the compound of formula IX (R=—COR'), for the cyclisation of the N,N'-bisformyl derivatives. Particularly suitable $NH_3$ donors are salts of ammonia with weak acids, e.g. carboxylic acids. Preferred salts are ammonium carbonate, ammonium bicarbonate or ammonium formate. The reaction temperature for the cyclisation of the N,N'-bisformyl derivatives is normally in the range from 50° to 200° C., preferably from 120° to 180° C.

All the above described ketalisation reactions of a ketone with a substituted α, β-diol or α, γ-diol result in the formation primarily of mixtures of diastereoisomers of the compounds of formula I. The compounds of formula I may be obtained e.g. in the following two diasteroisomeric forms, namely A and B types:

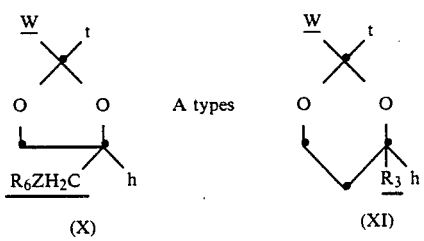

The configuration of the A type shall be designated here and subsequently as the "trans"-isomer or "trans-racemate":

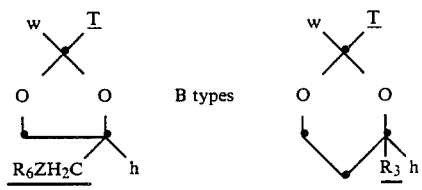

wherein w and W are the group

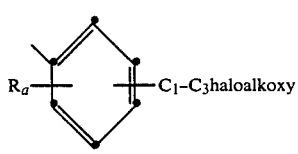

and t and T are the group

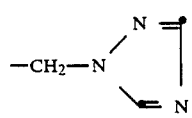

and the underlined symbols W, T, $R_3$ and $R_6ZH_2C$— in the three-dimensional structures reproduced above denote groupings in front of the drawing plane, and the lower-case symbols t, w and h (=hydrogen) denote groupings behind the drawing plane.

The configuration of type B will be correspondingly designated as "cis"-isomer, "cis-racemate". The separation of the two diastereoisomers may be effected e.g. by fractional crystallisation or by chromatography (thin-layer chromatography), column chromatography, liquid high-pressure chromatography and the like). The preparation of the optically pure isomers is also possible. The compound 1.3 illustrated below may serve as an example.

Starting from the two optically active 1,2-butanediols, the four isomers can be prepared as follows:

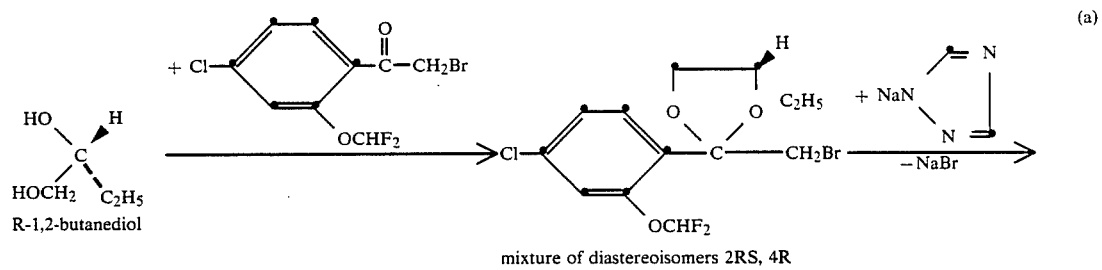

(a)

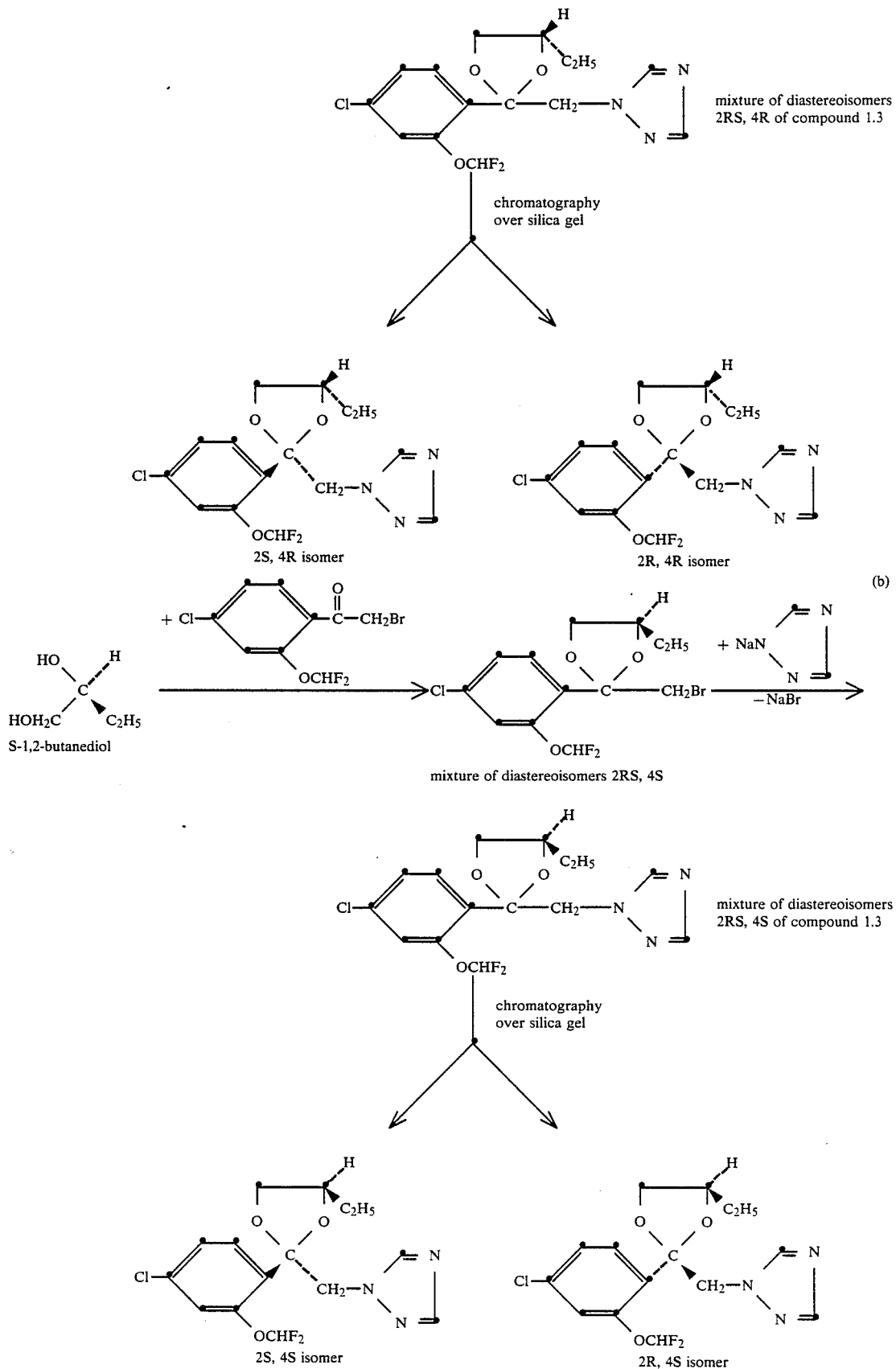

The four isomers differ in fungicidal activity and the differences depend on the different species of fungi. In this connection, the 2S-configuration with the cis-arrangement of ethyl and triazolylmethyl (2S, 4R isomer) is the somewhat more active form.

The two "trans- and cis"-racemates also have different biological activity. As a rule, the mixtures of diastereoisomers will, for practical purposes, be used as obtained from the synthesis without resolution.

The invention relates to all isomeric compounds of formula I in the pure form or in any ratio to one another, as well as to the salts and metal complex salts thereof.

The process for the preparation of compounds of formula I as described in variants A, B, C and D likewise constitutes an object of the invention.

The intermediates of formula III, wherein $R_a$, U and V are as defined for formula I and X is halogen, benzenesulfonyloxy, p-tosyloxy, trifluoroacetyloxy or lower alkylsulfonyloxy, and the preparation thereof, constitute a further object of the invention.

Compounds of formula III can be obtained by ketalisation of a suitably substituted acetophenone derivative of formula XII

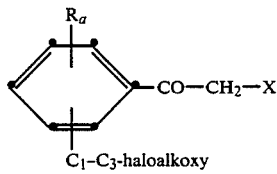

(XII)

The ketalisation is effected with a monohydric alochol U—OH (or V—OH) or with a dihydric alochol HO—U—V—OH, wherein $R_a$, X, U and V are as defined for formula I, in the presence of a strong acid such as toluenesulfonic acid and in an inert solvent such as a hydrocarbon.

The intermediates of formula XII can be prepared by methods which are known per se by halogenation, e.g. bromination with $Br_2$, of the side chain of the $C_1$-$C_3$-haloalkoxyacetophenone derivative (obtained from a haloalkane, e.g. freon, and the 2-hydroxy- and/or 4-hydroxyacetophenone derivative).

The ketones employed as intermediates of formula IV constitute a further object of the invention.

Surprisingly, it has been found that compounds of formula I have for practical purposes a very useful microbicidal spectrum against phytopathogenic fungi and bacteria. They have very useful curative, preventive and systemic properties and can be used for protecting cultivated plants. With the compounds of formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Ascomycetes (e.g. Venturia, Podosphaera, Erysiphe, Monilinia, Uncinula): Basidiomycetes (e.g. the genera Hemileia, Rhizoctonia, Puccinia); Fungi imperfecti (e.g. Botrytis, Helminthosporium, Fusarium, Septoria, Cercospora, Alternaria and, especially, Pyricularia). In addition, the compounds of formula I have a systemic action. They can also be used as seed dressing agents for protecting seeds (fruit, tubers, grains) and plant cuttings against fungus infections as well as against phytopathogenic fungi which occur in the soil. The compounds of the invention are especially well tolerated by plants and they are ecologically non-harmful as their presence in the soil is no longer detectable even after one growing season. Further, the pronounced activity of the compounds of formula I against pathogens in rice, e.g. Pyricularia and Pellicularia, merits particular mention. The advantage of the compounds of formula I resides chiefly in the feature that they are able to control an already existing infestation (curative action) with unexpected effectiveness. This property has the exceptional advantage in actual practice that it is not necessary to treat crops such as cereals and rice prophylactically and that treatment need not be effected until the first signs of infestation with e.g. Pyricularia on rice appear.

Accordingly, the invention also relates to microbicidal compositions and to the use of compounds of the formula I for controlling phytopathogenic microorganisms, especially harmful fungi, and for the preventive treatment of plants to protect them from attack by such microorganisms.

The invention further embraces the preparation of agrochemical compositions, which comprises homogeneously mixing the active ingredient with one or more compounds or groups of compounds described herein. The invention furthermore relates to a method of treating plants, which comprises applying thereto the compounds of the formula I or the novel compositions.

Without implying any limitation, target crops to be protected within the scops of the present invention comprise e.g. the following species of plants:

cereals (wheat, barley, rye, oats, rice, sorghum and related crops), beet (sugar beet and fodder beet), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers).

The compounds of formula I are normally applied in the form of compositions and can be applied to the crop area or plant to be treated, simultaneously or in succession, with further compounds. These compounds can be fertilisers or micronutrient donors as well as other preparations that influence plant growth. They can also be selective herbicides, fungicides, bactericides, nematicides, molluscicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I or an agrochemical composition which contains at least one of said compounds, is application to the growing parts of plants, especially the leaves (foliar application). The number of applications and the rate of application depend on the biological and climatic life conditions of the pathogen (type of fungus). However, the compound of formula I can also penetrate the plant through the roots via the soil (systemic action) by drenching the locus of the plant with a liquid formulation, or by applying the compounds in solid form to the soil, e.g. in granular form (soil application). The compounds of formula I may also be applied to seeds (coating) by impregnating the seeds either with a liquid formulation containing a compound of the formula I, or coating them with a solid formulation. In special cases, further types of application are also possible, e.g. selective treatment of the buds or fruit.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 100 g to 600 g a.i./ha.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl gylcerol, lysolecithin, plasmalogenes or cardiolipin, which can be obtained e.g. from animal or plant cells, in particular from the brain, heart, liver, egg yokes or soya beans. Exmaples of useful physical forms are phosphatidyl choline mixtures. Examples of synthetic phospholipids are dioctanoylphosphatidyl choline and dipalmitoylphosphatidyl choline.

Depending on the nature of the compound of the formula I to be formulated, suitable surface-active compounds are nonionic, cationic and/or anionic sufactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaruin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_{8-14}$ 1$_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensate. Also suitable are corresponding phosphates, e.g. salts of the phosphated adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids, and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are known to the skilled person and described e.g. in "McCutcheon's Detergents and Emulsifiers Annual", MC Publishing Corp. Ringwood, N.J., 1981; Helmut Stache, "Tensid-Taschenbuch" (Surfactant Handbook) Carl Hanser Verlag, Munich/Vienna, 1981.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients such as stabilisers, antifoams, viscosity regulators, binders, tackifiers as well as fertilisers or other active ingredients for obtaining special effects.

Such agrochemical compositions also constitute an object of the present invention.

The invention is illustrated in more detail by the following Examples, without implying any restriction to what is described therein. Parts and percentages are by weight. $C_6H_5$ is a phenyl group.

1. PREPARATORY EXAMPLES

EXAMPLE 1.1

Preparation of

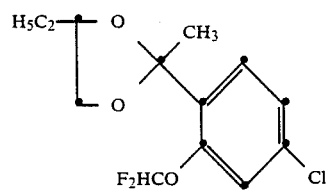

(compound 1.3)

2-[2'-Difluoromethoxy-4'-chlorophenyl]-2-(1H-1,2,4-triazolylmethyl)-4-ethyl-1,3-dioxolane (A) Synthesis of the intermediates (a) Preparation of

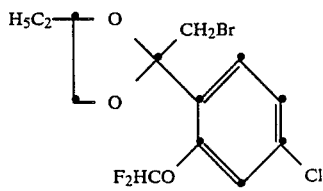

2-[2'-Difluoromethoxy-4'-chlorophenyl]-2-methyl-4-ethyl-1,3-dioxolane 12.8 parts of 1-(4-chloro-2-difluoromethoxyphenyl)ethan-1-one and 10.4 parts of 1,2-butanediol are heated under reflux for 12 hours in 100 ml of abs. toluene in the presence of 0.2 part of p-toluenesulfonic acid as catalyst, while removing the water of reaction with a water separator. The reaction mixture is cooled to room temperature and then washed with 2×100 ml of water, dried over sodium sulfate and filtered. The solvent is removed by evaporation and the residual oil is purified by high-vacuum distillation; b.p. 78°–80° C./0.04 mbar.

(b) Preparation of

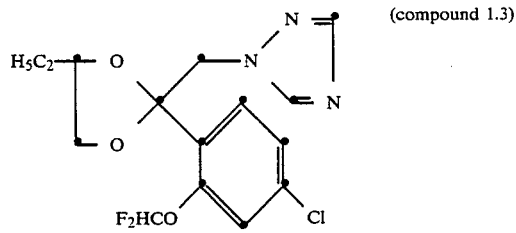

2-[2'-Difluoromethoxy-4'-chlorophenyl]-2-bromoethyl-4-ethyl-1,3-dioxolane 12.7 parts of the 2-(4'-chloro-2'-difluoromethoxyphenyl)-2-methyl-4-ethyl-1,3-dioxolane prepared in (a) are dissolved in 100 ml of abs. chloroform and the solution is warmed to 30° C. Under irradiation with a 150 watt spot lamp, 7.3 parts of bromine in 30 ml of abs. chloroform are added dropwise over 1 hour and the reaction mixture is then stirred for 2 hours at room temperature. The reaction mixture is then washed with 2×100 ml of water, dried over sodium sulfate, and filtered. The solvent is removed by evaporation and the oily residue is purified by high vacuum distillation; b.p. 113°–115° C./0.05 mbar.

(B) Synthesis of the final product 5.9 parts of 1,2,4-triazole sodium salt, a catalytic amount of potassium iodide and 12 parts of the 2-(2'-difluoromethoxy-4'-chlorophenyl)-2-bromomethyl-4-ethyl-1,3-dioxolane prepared in (b) are stirred in 100 ml of dimethylformamide for 16 hours at a bath temperature of 130° C. The reaction mixture is cooled to room temperature, poured into 500 ml of water and extracted with 2×300 ml of diethyl ether. The combined organic phases are washed with 2×200 ml of water, dried over sodium sulfate, filtered, and the solvent is removed by evaporation. The oily residue is chromatographed through a 50 cm column of silica gel with a 1:1 mixture of methylene chloride/diethyl ether as eluant. The eluant is removed by evaporation to give a yellow oil with a refractive index $n_D^{27}$: 1.5132.

EXAMPLE 1.2

Preparation of

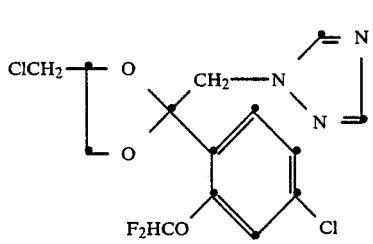 (compound 1.59)

2-[2'-Difluoromethoxy-4'-chlorophenyl]-2-[1H-1,2,4-triazolylmethyl]-4-chloromethyl-1,3-dioxolane 14.2 parts of 1-(4-chloro-2-difluromethoxyphenyl)-2-(1H-1,2,4-triazolyl)ethan-1-one and 100 ml of n-butanol in 450 ml of abs. toluene are heated in the presence of 9.4 parts of p-toluenesulfonic acid for 5 hours under reflux, while removing the water of reaction with a water separator. After cooling to 60° C., 33 parts of 3-chloro1,2-propanediol and a further 18 parts of p-toluenesulfonic acid are added and the batch is refluxed for 80 hours while removing the water of reaction with a water separator. The reaction mixture is cooled to room temperature, washed twice with saturated aqueous sodium carbonate solution and with 2×200 ml of water, dried over sodium sulfate and filtered. The solvent is removed in a rotary evaporator and the oily residue is chromatographed through a 50 cm column of silica gel with a 1:1 mixture of methylene chloride/diethyl ether as eluant. The solvent mixture is removed by evaporation, affording the title compound in the form of a pale yellow oil with a refractive index $n_D^{22}$: 1.5336.

The following intermediates of formula IV can be employed:

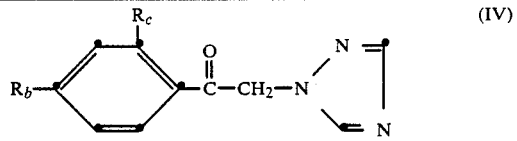 (IV)

| $R_c$ | $R_b$ | Physical data (°C.) |
|---|---|---|
| —OCHF$_3$ | Cl | m.p. 97–102° |
| Cl | —OCHF$_2$ | m.p. 67–69° |
| CH$_3$ | —OCHF$_2$ | m.p. 52–57° |
| —OCHF$_2$ | Br | m.p. 85–92° |
| —OCHF$_2$ | F | m.p. 106–113° (dec.) |

The following intermediates of formula III can be also be prepared in analogous manner (mixtures of diastereoisomers in varying ratios, unless otherwise indicated):

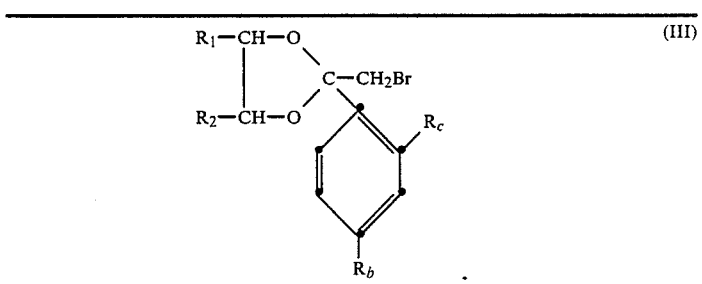 (III)

| $R_1$ | $R_2$ | $R_c$ | $R_b$ | Physical data (°C.) |
|---|---|---|---|---|
| —C$_3$H$_7$-n | H | —OCHF$_2$ | Br | b.p.: 124–126°/ 0.002 mbar |
| —C$_2$H$_5$ | H | CH$_3$ | —OCF$_2$CHCl$_2$ | $n_D^{24}$: 1.5171 |
| —C$_3$H$_7$-n | H | CH$_3$ | —OCF$_2$CCl$_2$F | $n_d^{23}$: 1.4981 |
| CH$_3$ | CH$_3$ | —OCHF$_2$ | Br | b.p.: 114–115°/ 0.02 mbar |
| —C$_3$H$_7$-n | H | CH$_3$ | —OCF$_2$CHCl$_2$ | $n_D^{24}$: 1.5145 |
| cyclohexyl | H | —OCHF$_2$ | Cl | b.p.: 143–149°/ 0.002 mbar |
| CH$_3$ | H | CH$_3$ | —OCF$_2$CHClF | $n_D^{24}$: 1.5024 |
| —C$_2$H$_5$ | H | CH$_3$ | —OCF$_2$CHF$_2$ | $n_D^{24}$: 1.4828 |
| CH$_3$ | H | —OCHF$_2$ | Br | $n_D^{28}$: 1.5212 |
| —C$_3$H$_7$-n | H | CH$_3$ | —OCF$_2$CHF$_2$ | $n_D^{25}$: 1.4813 |
| —C$_2$H$_5$ | H | CH$_3$ | —OCF$_2$CHClF | $n_D^{24}$: 1.5002 |
| —CH$_2$OCH$_3$ | H | CH$_3$ | —OCF$_2$CHF$_2$ | $n_D^{24}$: 1.4848 |
| —CH$_2$OCH$_2$CF$_3$ | H | —OCHF$_2$ | Br | b.p.: 118–121°/ 0.02 mbar |
| CH$_3$ | H | CH$_3$ | —OCF$_2$CHFCF$_3$ | $n_D^{24}$: 1.4544 |
| —C$_3$H$_7$-n | H | CH$_3$ | —OCF$_2$CHClF | $n_D^{24}$: 1.4972 |
| —C$_2$H$_5$ | H | CH$_3$ | —OCF$_2$CHFCF$_3$ | $n_D^{24}$: 1.4649 |
| CH$_3$ | H | CH$_3$ | —OCHF$_2$ | $n_d^{23}$: 1.5142 |
| —C$_3$H$_7$-n | H | CH$_3$ | —OCHF$_2$ | $n_D^{23}$: 1.5056 |
| —CH$_2$OC$_4$H$_9$-sec. | H | —OCHF$_2$ | Cl | $n_D^{28}$: 1.5011 |

(III)

| $R_1$ | $R_2$ | $R_c$ | $R_b$ | Physical data (°C.) |
|---|---|---|---|---|
| $CH_3$ | $CH_3$ | $CH_3$ | $-OCHF_2$ | $n_D^{23}$: 1.5086 |
| $-C_3H_7$-n | H | $CH_3$ | $-OCF_2CHCF_3$ | $n_D^{24}$: 1.4635 |
| cyclohexyl | H | $-OCHF_2$ | Br | $n_D^{26}$: 1.5676 |
| $-CH_2OCH_3$ | H | $CH_3$ | $-OCF_2CHClF$ | $n_D^{25}$: 1.5102 |
| $-CH_2OCH_2CF_3$ | H | $-OCHF_2$ | Cl | $n_D^{28}$: 1.4844 |
| $CH_3$ | H | $CH_3$ | $-OCF_2CCl_2F$ | $n_D^{23}$: 1.5022 |
| $-C_2H_5$ | H | $CH_3$ | $-OCF_2CCl_2F$ | b.p.: 135–136°/0.02 mbar |
| $-CH_2OCH_3$ | H | $CH_3$ | $OCF_2CHFCF_3$ | $n_D^{23}$: 1.4668 |
| $-C_2H_5$ | H | $-OCHF_2$ | Br | b.p.: 113–115°/0.02 mbar |
| $CH_3$ | H | Cl | $-OCHF_2$ | $n_d^{24}$: 1.5234 |
| $-C_2H_5$ | H | Cl | $-OCHF_2$ | $n_D^{24}$: 1.5173 |
| $-CH_2OCH_3$ | H | $CH_3$ | $-OCF_2CCl_2F$ | $n_D^{23}$: 1.5012 |
| $-C_3H_7$-n | H | Cl | $-OCHF_2$ | $n_d^{22}$: 1.5126 |
| $-CH_2OCH_3$ | H | Cl | $-OCHF_2$ | m.p.: 75–78° |
| $-CH_2OCH_3$ | H | $CH_3$ | $-OCF_2CHCl_2$ | $n_D^{22}$: 1.5176 |
| $CH_3$ | H | $CH_3$ | $-OCF_2CHF_2$ | $n_D^{25}$: 1.4852 |
| $CH_3$ | $CH_3$ | $-OCHF_2$ | F | $n_D^{26}$: 1.4886 |
| $-C_2H_5$ | H | $-OCHF_2$ | $-OCHF_2$ | b.p.: 116–117°/0.04 mbar |
| $-CH_2OCH_3$ | H | $-OCHF_2$ | Cl | b.p.: 107–109°/0.05 mbar |
| $CH_3$ | $-C_2H_5$ | $CH_3$ | $-OCHF_2$ | $n_D^{23}$: 1.5030 |
| $CH_3$ | $-C_2H_5$ | $-OCHF_2$ | F | $n_D^{25}$: 1.4859 |
| $-C_2H_5$ | H | $-OCHF_2$ | Cl | b.p.: 113–115°/0.05 mbar |
| $-CH_2OCH_2C\equiv CH$ | H | $-OCHF_2$ | Cl | $n_D^{27}$: 1.4931 |
| $-C_3H_7$-n | H | $-OCHF_2$ | $-OCHF_2$ | b.p.: 125–126°/0.05 mbar |
| $-C_2H_5$ | H | $CH_3$ | $-OCHF_2$ | b.p.: 105–108°/0.04 mbar |
| $CH_3$ | H | $-OCHF_2$ | F | $n_D^{26}$: 1.4931 |
| $-CH_2OCH_3$ | H | $-OCHF_2$ | F | $n_D^{26}$: 1.4918 |
| $CH_3$ | H | $-OCHF_2$ | Cl | $n_D^{24}$: 1.4976 |
| $-C_2H_5$ | H | $-OCHF_2$ | F | $n_D^{26}$: 1.4885 |
| $-C_3H_7$-n | H | $-OCHF_2$ | Cl | $n_D^{23}$: 1.4899 |
| $CH_3$ | $CH_3$ | $-OCHF_2$ | $-OCHF_2$ | b.p.: 100–102°/0.04 mbar |
| $CH_3$ | $CH_3$ | $-OCHF_2$ | Cl | b.p.: 107–112°/0.04 mbar |
| $-C_3H_7$-n | H | $-OCHF_2$ | F | $n_D^{26}$: 1.4881 |

The following intermediates of formula III can also be prepared in analogous manner (mixtures of diastereoisomers in varying ratios, unless otherwise indicated):

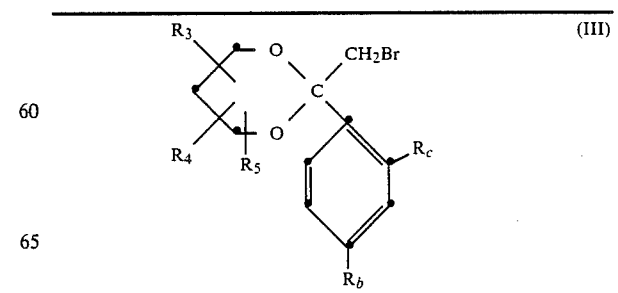

(III)

| $R_3$ | $R_4$ | $R_5$ | $R_c$ | $R_b$ | Physical data (°C.) |
|---|---|---|---|---|---|

| | | | | | |
|---|---|---|---|---|---|
| 4-CH$_3$ | H | H | —OCHF$_2$ | F | $n_D^{22}$: 1.5006 |
| 5-CH$_3$ | 5-CH$_3$ | H | —OCHF$_2$ | F | $n_D^{25}$: 1.4937 |
| 4-CH$_3$ | H | H | —OCHF$_2$ | Br | $n_D^{28}$: 1.5197 |
| 4-CH$_3$ | H | H | —OCHF$_2$ | Cl | b.p.: 113–116°/0.09 mbar |
| 5-CH$_3$ | 5-CH$_3$ | H | —OCHF$_2$ | Br | $n_D^{26}$: 1.5136 |
| 4-CH$_3$ | H | H | —OCHF$_2$ | —OCHF$_2$ | b.p.: 125–127°/0.07 mbar |
| 5-CH$_3$ | 5-CH$_3$ | H | —OCHF$_2$ | Cl | $n_D^{23}$: 1.4997 |
| 4-CH$_3$ | H | H | Cl | —OCHF$_2$ | $n_D^{22}$: 1.5089 |
| 4-CH$_3$ | H | H | CH$_3$ | —OCHF$_2$ | $n_D^{23}$: 1.5048 |
| H | H | H | Cl | —OCHF$_2$ | $n_D^{25}$: 1.4987 |
| 5-CH$_3$ | 5-CH$_3$ | H | Cl | —OCHF$_2$ | $n_D^{22}$: 1.5173 |
| 5-CH$_3$ | 5-CH$_3$ | H | CH$_3$ | —OCHF$_2$ | $n_D^{24}$: 1.5097 |
| 4-CH$_3$ | H | H | Br | —OCHF$_2$ | b.p.: 109–111°/0.05 mbar |

The following compounds of formula I can be prepared in accordance with Example 1.1 or 1.2 or by one of the other methods described above (mixtures of diastereoisomers in varying ratios, unless otherwise indicated):

TABLE 1

Compounds of formula

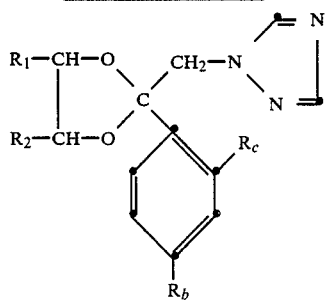

| Comp. | R$_1$ | R$_2$ | R$_c$ | R$_b$ | Salt | Physical data |
|---|---|---|---|---|---|---|
| 1.1 | CH$_3$ | H | CH$_3$ | —OCF$_2$CHF$_2$ | — | $n_D^{24}$: 1.4868 |
| 1.2 | —C$_3$H$_7$-n | H | —OCHF$_2$ | —OCHF$_2$ | — | $n_D^{23}$: 1.4841 |
| 1.3 | —C$_2$H$_5$ | H | —OCHF$_2$ | Cl | — | $n_D^{27}$: 1.5132 |
| 1.4 | —C$_2$H$_5$ | H | CH$_3$ | —OCHF$_2$ | — | $n_D^{28}$: 1.5067 |
| 1.5 | —C$_2$H$_5$ | H | CH$_3$ | —OCF$_2$CFCl$_2$ | HCl | |
| 1.6 | —C$_2$H$_5$ | H | —OCHF$_2$ | —OCHF$_2$ | — | $n_D^{23}$: 1.4860 |
| 1.7 | CH$_3$ | H | CH$_3$ | —OCF$_2$CHFCl | — | $n_D^{25}$: 1.4970 |
| 1.8 | CH$_3$ | CH$_3$ | —OCHF$_2$ | —OCHF$_2$ | — | $n_D^{28}$: 1.4856 |
| 1.9 | —CH$_2$OCH$_3$ | H | —OCHF$_2$ | Cl | — | $n_D^{22}$: 1.5164 |
| 1.10 | CH$_3$ | H | —OCHF$_2$ | F | — | |
| 1.11 | —C$_2$H$_5$ | H | CH$_3$ | —OCF$_2$CCl$_3$ | ·½ CaCl$_2$ | |
| 1.12 | —C$_3$H$_7$-n | H | —OCHF$_2$ | Cl | — | $n_D^{22}$: 1.5113 |
| 1.13 | CH$_3$ | CH$_3$ | —OCHF$_2$ | Cl | — | $n_D^{22}$: 1.5150 |
| 1.14 | CH$_3$ | H | CH$_3$ | —OCF$_2$CHCl$_2$ | HNO$_3$ | |
| 1.15 | —C$_3$H$_7$-n | H | —OCHF$_2$ | F | — | $n_D^{23}$: 1.4901 |
| 1.16 | CH$_3$ | CH$_3$ | CH$_3$ | —OCHF$_2$ | — | $n_D^{23}$: 1.5070 |
| 1.17 | —C$_2$H$_5$ | H | Cl | —OCF$_2$CHFBr | — | |
| 1.18 | —CH$_2$OCH$_3$ | H | —OCHF$_2$ | F | — | |
| 1.19 | —C$_3$H$_7$-n | H | CH$_3$ | —OCHF$_2$ | — | $n_D^{23}$: 1.5050 |
| 1.20 | CH$_3$ | H | Cl | —OCH$_2$CF$_3$ | — | |
| 1.21 | CH$_3$ | H | CH$_3$ | —OCHF$_2$ | — | $n_D^{23}$: 1.5116 |
| 1.22 | —CH$_2$OC$_2$H$_5$ | H | —OCHF$_2$ | F | ·HNO$_3$ | |
| 1.23 | CH$_3$ | H | —OCHF$_2$ | Br | — | $n_D^{26}$: 1.5292 |
| 1.24 | —C$_2$H$_5$ | H | Cl | —OCH$_2$CH$_2$Cl | — | |
| 1.25 | —CH$_2$OCH$_2$CF$_3$ | H | —OCHF$_2$ | F | — | $n_D^{25}$: 1.5137 |
| 1.26 | (4-Cl-phenyl) | H | CH$_3$ | —OCHF$_2$ | — | |
| 1.27 | —C$_2$H$_5$ | H | —OCHF$_2$ | Br | — | $n_D^{25}$: 1.5266 |
| 1.28 | CH$_3$ | H | Cl | —OCH$_2$CH$_2$F | — | |
| 1.29 | —CH$_2$O-(4-Cl-phenyl) | H | CH$_3$ | —OCHF$_2$ | — | |
| 1.30 | —C$_2$H$_5$ | H | Cl | —OCH$_2$CCl$_3$ | — | |
| 1.31 | —CH$_2$OCH$_2$CH=CH$_2$ | H | —OCHF$_2$ | F | — | |

TABLE 1-continued

Compounds of formula

| Comp. | R₁ | R₂ | $R_c$ | $R_b$ | Salt | Physical data |
|---|---|---|---|---|---|---|
| 1.32 | —C₃H₇-n | H | —OCHF₂ | Br | — | $n_D^{24}$: 1.5301 |
| 1.33 | CH₃ | H | Cl | —OCCl₃ | ½ CuCl₂ | |
| 1.34 | —CH₂OH | H | CH₃ | —OCHF₂ | — | |
| 1.35 | —CH₂SC₂H₅ | H | CH₃ | —OCHF₂ | — | |
| 1.36 | —CH₂OCH₂C≡CH | H | CH₃ | —OCHF₂ | — | $n_D^{26}$: 1.5138 |
| 1.37 | —C₂H₅ | H | Cl | —OCBr₃ | — | |
| 1.38 | —C₃H₇-i | H | —OCHF₂ | Br | — | |
| 1.39 | CH₃ | H | Cl | —OCF₂Br | — | |
| 1.40 | CH₃ | —C₂H₅ | —OCHF₂ | F | — | $n_D^{23}$: 1.5137 |
| 1.41 | CH₃ | —C₂H₅ | CH₃ | —OCHF₂ | — | $n_D^{23}$: 1.5034 |
| 1.42 | —C₂H₅ | H | Cl | —OC₂F₅ | — | |
| 1.43 | —CH₂OCH₃ | H | CH₃ | —OCHF₂ | — | |
| 1.44 | CH₃ | H | F | —OCHF₂ | — | |
| 1.45 | H | H | Cl | —OCHF₂ | — | |
| 1.46 | CH₃ | H | Cl | —OCH₂Cl | — | |
| 1.47 | H | H | —OCHF₂ | Cl | — | |
| 1.48 | CH₃ | —C₂H₅ | —OCHF₂ | F | — | |
| 1.49 | —CH₂OCH₃ | H | —OCHF₂ | Br | — | |
| 1.50 | —C₂H₅ | H | Cl | —OCHFCl | — | |
| 1.51 | —CH₂OC₂H₅ | H | —OCHF₂ | Br | — | |
| 1.52 | CH₃ | H | —OCHF₂ | Cl | — | $n_D^{26}$: 1.5180 |
| 1.53 | CH₃ | H | Cl | —OCH₂Br | — | |
| 1.54 | —C₆H₁₃-n | H | —OCHF₂ | Cl | — | |
| 1.55 | —CH₂OCH₂CF₃ | H | —OCHF₂ | Br | — | $n_D^{26}$: 1.4982 |
| 1.56 | —CH₂OC₂H₅ | H | CH₃ | —OCHF₂ | — | |
| 1.57 | —CH₂SC₃H₇-i | H | CH₃ | —OCHF₂ | — | |
| 1.58 | —C₂H₅ | H | F | —OCHF₂ | — | |
| 1.59 | —CH₂Cl | H | —OCHF₂ | Cl | — | $n_D^{22}$: 1.5336 |
| 1.60 | (phenyl ring: R₁ and R₂ together form a fused benzene ring) | H | —OCHF₂ | Cl | — | $n_D^{23}$: 1.5570 |
| 1.61 | —CH₂OCH₂CH=CH₂ | H | —OCHF₂ | Br | — | |
| 1.62 | —C₃H₇-n | H | F | —OCHF₂ | — | |
| 1.63 | —CH₂OC₂H₅ | H | —OCHF₂ | Cl | — | |
| 1.64 | —CH₂O(CH₂)₃OCH₃ | H | CH₃ | —OCHF₂ | — | |
| 1.65 | CH₃ | —C₂H₅ | —OCHF₂ | Br | — | |
| 1.66 | —CH₂OC₃H₇-n | H | CH₃ | —OCHF₂ | — | |
| 1.67 | —CH₂OCH₃ | H | F | —OCHF₂ | — | |
| 1.68 | CH₃ | H | Cl | —OCHF₂ | — | $n_D^{28}$: 1,5208 |
| 1.69 | —CH₂OCH₂CF₃ | H | —OCHF₂ | Cl | — | $n_D^{24}$: 1.4876 |
| 1.70 | —CH₂OCH₃ | H | —OCHF₂ | —OCHF₂ | — | |
| 1.71 | —CH₂OC₂H₅ | H | F | —OCHF₂ | — | |
| 1.72 | CH₃ | CH₃ | —OCHF₂ | Br | — | $n_D^{26}$: 1.5268 |
| 1.73 | —CH₂OC₃H₇-i | H | CH₃ | —OCHF₂ | — | |
| 1.74 | —CH₂OCH₂CF₃ | H | F | —OCHF₂ | — | |
| 1.75 | —CH₂OCH₂CH=CH₂ | H | —OCHF₂ | Cl | — | |
| 1.76 | —CH₂OC₂H₅ | H | —OCHF₂ | —OCHF₂ | — | |
| 1.77 | —C₂H₅ | H | Cl | —OCHF₂ | — | $n_D^{29}$: 1.5159 |
| 1.78 | —CH₂OCH₂CF₃ | H | —OCHF₂ | —OCHF₂ | — | |
| 1.79 | —CH₂OCH₂—C≡CH | H | —OCHF₂ | Cl | — | |
| 1.80 | CH₃ | —C₂H₅ | F | —OCHF₂ | — | |
| 1.81 | —C₃H₇-n | H | Cl | —OCHF₂ | — | $n_D^{28}$: 1.5123 |
| 1.82 | —CH₂OC₆H₁₃-n | H | CH₃ | —OCHF₂ | — | |
| 1.83 | —C₃H₇-i | H | Cl | —OCHF₂ | — | |
| 1.84 | CH₃ | —C₂H₅ | —OCHF₂ | Cl | — | |
| 1.85 | —CH₂OCH₂CH=CH₂ | H | —OCHF₂ | —OCHF₂ | — | |
| 1.86 | CH₃ | —C₂H₅ | —OCHF₂ | —OCHF₂ | — | |
| 1.87 | —CH₂OCH₂CF₃ | H | CH₃ | —OCHF₂ | — | |
| 1.88 | —C₃H₇-i | H | CH₃ | —OCHF₂ | — | |
| 1.89 | CH₃ | CH₃ | F | —OCHF₂ | — | |

TABLE 1-continued

Compounds of formula

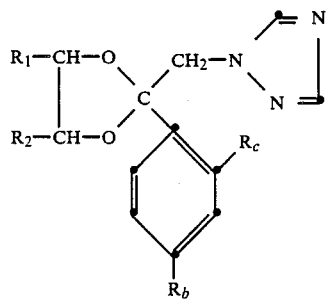

| Comp. | $R_1$ | $R_2$ | $R_c$ | $R_b$ | Salt | Physical data |
|---|---|---|---|---|---|---|
| 1.90 | —$CH_2OCH_3$ | H | Cl | —$OCHF_2$ | — | $n_D^{27}$: 1.5185 |
| 1.91 | —$CH_2OCH_2CH=CH_2$ | H | $CH_3$ | —$OCHF_2$ | — | |
| 1.92 | —$C_3H_{13}$-n | H | $CH_3$ | —$OCHF_2$ | — | |
| 1.93 | —$CH_2OC_2H_5$ | H | Cl | —$OCHF_2$ | — | |
| 1.94 | —$CH_2OCH_2C\equiv CH$ | H | $CH_3$ | —$OCHF_2$ | — | |
| 1.95 | —$CH_2OCH_2CF_3$ | H | Cl | —$OCHF_2$ | — | |
| 1.96 | —$C_3H_7$-i | H | Br | —$OCHF_2$ | — | |
| 1.97 | —$CH_2Cl$ | H | $CH_3$ | —$OCHF_2$ | — | $n_D^{25}$: 1.4936 |
| 1.98 | —$CH_2OCH_3$ | H | Br | —$OCHF_2$ | — | |
| 1.99 | —$CH_2O$—⌬ | H | $CH_3$ | —$OCHF_2$ | — | |
| 1.100 | ⌬ | H | $CH_3$ | —$OCHF_2$ | — | |
| 1.101 | —$CH_2OC_2H_5$ | H | Br | —$OCHF_2$ | — | |
| 1.102 | —$CH_2OCH_2CH=CH_2$ | H | Cl | —$OCHF_2$ | — | |
| 1.103 | $CH_3$ | —$C_2H_5$ | Br | —$OCHF_2$ | — | |
| 1.104 | —$C_3H_7$-n | H | Cl | —$OCF_2CFCl_2$ | — | $n_D^{25}$: 1.5139 |
| 1.105 | —$CH_2OCH_2C\equiv CH$ | H | Br | —$OCHF_2$ | — | |
| 1.106 | —$CH_2OCH_2C\equiv CH$ | H | Cl | —$OCHF_2$ | — | |
| 1.107 | $CH_3$ | $CH_3$ | Br | —$OCHF_2$ | — | |
| 1.108 | $CH_3$ | —$C_2H_5$ | Cl | —$OCHF_2$ | — | |
| 1.109 | —$CH_2OCH_3$ | H | Cl | —$OCF_2CFCl_2$ | — | |
| 1.110 | $CH_3$ | $CH_3$ | Cl | —$OCHF_2$ | — | |
| 1.111 | —$C_3H_7$-n | H | Br | —$OCHF_2$ | — | |
| 1.112 | H | H | Br | —$OCHF_2$ | — | |
| 1.113 | —$CH_2OCH_2CF_3$ | H | Br | —$OCHF_2$ | — | |
| 1.114 | —$C_3H_7$-n | H | $CH_3$ | —$OCF_2CFCl_2$ | — | $n_D^{23}$: 1.4981 |
| 1.115 | $CH_3$ | H | Br | —$OCHF_2$ | — | |
| 1.116 | —$CH_2OCH_3$ | H | $CH_3$ | —$OCF_2CFCl_2$ | — | $n_D^{23}$: 1.5025 |
| 1.117 | —$C_2H_5$ | H | Br | —$OCHF_2$ | — | |
| 1.118 | —$C_3H_7$-n | H | $CH_3$ | —$OCF_2CHF_2$ | — | $n_D^{25}$: 1.4816 |
| 1.119 | —$CH_2OCH_3$ | H | $CH_3$ | —$OCF_2CHClF$ | — | $n_D^{23}$: 1.5047 |
| 1.120 | —$C_2H_5$ | H | $CH_3$ | —$OCF_2CHF_2$ | — | $n_D^{24}$: 1.4833 |
| 1.121 | —$C_2H_5$ | H | $CH_3$ | —$OCF_2CHClF$ | — | $n_D^{24}$: 1.4974 |
| 1.122 | —$CH_2OCH_3$ | H | $CH_3$ | —$OCF_2CHF_2$ | — | $n_D^{25}$: 1.4868 |
| 1.123 | —$C_3H_7$-n | H | $CH_3$ | —$OCF_2CHClF$ | — | $n_D^{24}$: 1.4955 |
| 1.124 | —$CH_2F$ | H | —$OCHF_2$ | Cl | — | $n_D^{24}$: 1.5397 |
| 1.125 | ⌬ | H | —$OCHF_2$ | Br | — | $n_D^{26}$: 1.5661 |
| 1.126 | —$CH_2F$ | H | Cl | —$OCHF_2$ | — | $n_D^{23}$: 1.5312 |
| 1.127 | —$CH_2Cl$ | H | Cl | —$OCHF_2$ | — | $n_D^{22}$: 1.5297 |
| 1.128 | $CH_3$ | H | $CH_3$ | —$OCF_2CFCl_2$ | — | $n_D^{23}$: 1.5033 |
| 1.129 | —$CH_2F$ | H | $CH_3$ | —$OCHF_2$ | — | $n_D^{24}$: 1.5288 |
| 1.130 | —$CH_2OC_4H_9$-sec. | H | —$OCHF_2$ | Cl | — | $n_D^{24}$: 1.5035 |
| 1.131 | —$C_2H_5$ | H | $CH_3$ | —$OCF_2CFCl_2$ | — | $n_D^{23}$: 1.5006 |
| 1.132 | —$CH_2OCH_2C\equiv CH$ | H | —$OCHF_2$ | Cl | — | $n_D^{23}$: 1.4983 |
| 1.133 | —$CH_2Cl$ | H | —$OCHF_2$ | Br | — | $n_D^{22}$: 1.5372 |
| 1.134 | —$CH_2F$ | H | —$OCHF_2$ | Br | — | $n_D^{24}$: 1.5293 |

TABLE 2
Compounds of formula

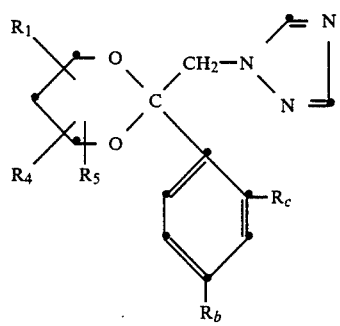

| Comp. | $R_3$ | $R_4$ | $R_5$ | $R_c$ | $R_b$ | Salt | Physical data |
|---|---|---|---|---|---|---|---|
| 2.1 | 4-$CH_3$ | H | H | $OCHF_2$ | F | $HNO_3$ | |
| 2.2 | 4-$CH_3$ | H | H | $OCHF_2$ | Cl | — | $n_D^{24}$: 1,4973 |
| 2.3 | 5-$C_2H_5$ | 5-$C_2H_5$ | H | $CH_3$ | —$OCHF_2$ | — | |
| 2.4 | 5-$CH_3$ | 5-$CH_3$ | H | —$OCHF_2$ | F | — | $n_D^{23}$: 1.5134 |
| 2.5 | 4-$CH_3$ | 5-$CH_3$ | 6-$CH_3$ | Cl | —$OCHF_2$ | — | |
| 2.6 | 4-$CH_3$ | H | H | $CH_3$ | —$OCF_2CHF_2$ | — | |
| 2.7 | 5-$CH_3$ | 5-$CH_3$ | H | $CH_3$ | —$OCF_2CHF_2$ | ½ $CuCl_2$ | |
| 2.8 | H | H | H | —$OCHF_2$ | Cl | — | |
| 2.9 | 5-$CH_3$ | 5-$C_3H_7$-n | H | $CH_3$ | —$OCHF_2$ | — | |
| 2.10 | 4-$CH_3$ | H | H | Cl | —$OCF_2CCl_3$ | $HNO_3$ | |
| 2.11 | 5-$CH_3$ | 5-$CH_3$ | H | —$OCHF_2$ | Cl | — | $n_D^{22}$: 1.5146 |
| 2.12 | 4-$CH_3$ | 6-$C_3H_7$-n | H | $CH_3$ | —$OCHF_2$ | — | |
| 2.13 | 5-$CH_3$ | 5-$CH_3$ | H | Cl | —$OCF_2CCl_3$ | — | |
| 2.14 | 4-$CH_3$ | H | H | —$OCHF_2$ | Br | — | $n_D^{24}$: 1.5234 |
| 2.15 | 4-$CH_3$ | H | H | F | —$OCHF_2$ | — | |
| 2.16 | H | H | H | Cl | —$OCF_2CFCl_2$ | — | |
| 2.17 | 5-$CH_3$ | 5-$CH_3$ | H | —$OCHF_2$ | Br | — | $n_D^{23}$: 1.5297 |
| 2.18 | 4-$CH_3$ | H | H | Cl | —$OCF_2CFCl_2$ | — | |
| 2.19 | H | H | H | $CH_3$ | —$OCF_3$ | — | |
| 2.20 | 5-$CH_3$ | 5-$CH_3$ | H | F | —$OCHF_2$ | — | |
| 2.21 | 4-$CH_3$ | H | H | —$OCHF_2$ | —$OCHF_2$ | — | $n_D^{25}$: 1.5173 |
| 2.22 | 5-$CH_3$ | 5-$CH_3$ | H | Cl | —$OCF_2CFCl_2$ | — | |
| 2.23 | H | H | H | Cl | —$OCHF_2$ | — | $n_D^{24}$: 1.4912 |
| 2.24 | 5-$CH_3$ | 5-$CH_3$ | H | —$OCHF_2$ | —$OCHF_2$ | — | |
| 2.25 | 5-$CH_3$ | 5-$CH_3$ | H | Br | —$OCHF_2$ | — | |
| 2.26 | 5-$CH_3$ | 5-$C_2H_5$ | H | Cl | —$OCF_2CFCl_2$ | — | |
| 2.27 | H | H | H | $CH_3$ | —$OCHF_2$ | — | |
| 2.28 | 4-$CH_3$ | H | H | Cl | —$OCHF_2$ | — | $n_D^{24}$: 1.4913 |
| 2.29 | 4-$CH_3$ | H | H | Cl | —$OCF_3$ | — | |
| 2.30 | 4-$CH_3$ | H | H | $CH_3$ | —$OCHF_2$ | — | $n_D^{25}$: 1.4897 |
| 2.31 | 4-$C_2H_5$ | H | H | $CH_3$ | —$OCHF_2$ | — | |
| 2.32 | 4-$CH_3$ | 4-$CH_3$ | H | Cl | —$OCHF_2$ | — | |
| 2.33 | 5-$CH_3$ | 5-$CH_3$ | H | Cl | —$OCF_3$ | — | $n_D^{23}$: 1.5092 |
| 2.34 | 5-$CH_3$ | 5-$CH_3$ | H | $CH_3$ | —$OCHF_2$ | — | $n_D^{25}$: 1.5176 |
| 2.35 | 5-$CH_3$ | 5-$C_2H_5$ | H | $CH_3$ | —$OCF_3$ | — | |
| 2.36 | 5-$CH_3$ | 5-$C_2H_5$ | H | Cl | —$OCHF_2$ | — | |
| 2.37 | 5-$CH_3$ | 5-$C_2H_5$ | H | $CH_3$ | —$OCHF_2$ | — | |
| 2.38 | 4-$CH_3$ | H | H | Br | —$OCHF_2$ | — | $n_D^{23}$: 1.5096 |
| 2.39 | 5-$CH_3$ | 5-$CH_3$ | H | Cl | —$OCHF_2$ | — | $n_D^{23}$: 1.5072 |

TABLE 3
Compounds of formula

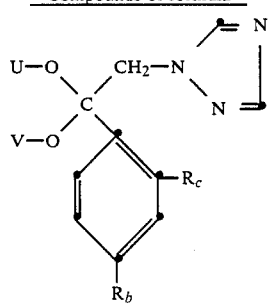

| Comp. | U | V | $R_c$ | $R_b$ | Salt | Physical data |
|---|---|---|---|---|---|---|
| 3.1 | $CH_3$ | $CH_3$ | —$OCHF_2$ | F | — | |
| 3.2 | $CH_3$ | $CH_3$ | $CH_3$ | —$OCHF_2$ | — | $n_D^{23}$: 1.5072 |

TABLE 3-continued

Compounds of formula

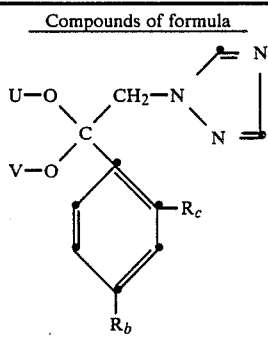

| Comp. | U | V | $R_c$ | $R_b$ | Salt | Physical data |
|---|---|---|---|---|---|---|
| 3.3 | $C_2H_5$ | $C_2H_5$ | $-OCHF_2$ | Cl | — | $n_D^{22}$: 1.5132 |
| 3.4 | $C_4H_9$ sec. | $C_4H_9$ sec. | $CH_3$ | $-OCHF_2$ | — | |
| 3.5 | $C_3H_7$-n | $C_3H_7$-n | $-OCHF_2$ | Cl | — | |
| 3.6 | $C_{12}H_{25}$-n | $C_{12}H_{25}$-n | $CH_3$ | $-OCHF_2$ | — | |
| 3.7 | $CH_3$ | $CH_3$ | $-OCHF_2$ | Br | — | $n_D^{25}$: 1.5176 |
| 3.8 | $C_4H_9$-n | $C_4H_9$-n | $CH_3$ | $-OCHF_2$ | — | |
| 3.9 | $-CH_2CF_3$ | $-CH_2CF_3$ | $-OCHF_2$ | $-OCHF_2$ | — | |
| 3.10 | $-CH_2CH_2Cl$ | $-CH_2CH_2Cl$ | $CH_3$ | $-OCHF_2$ | — | |
| 3.11 | $CH_3$ | $CH_3$ | F | $-OCHF_2$ | — | |
| 3.12 | $CH_3$ | $CH_3$ | Cl | $-OCHF_2$ | — | |
| 3.13 | $C_2H_5$ | $C_2H_5$ | Br | $-OCHF_2$ | — | |
| 3.14 | $C_3H_7$-i | $C_3H_7$-i | Cl | $-OCHF_2$ | — | $n_D^{25}$: 1.5112 |
| 3.15 | $C_3H_7$-i | $C_3H_7$-i | $-OCHF_2$ | Cl | — | |
| 3.16 | $C_4H_9$ sec. | $C_4H_9$ sec. | Cl | $-OCHF_2$ | — | |
| 3.17 | $C_4H_9$-i | $C_4H_9$-i | Cl | $-OCHF_2$ | — | |

FORMULATION EXAMPLES

2. Formulation Examples for liquid active ingredients of the formula I (throughout, percentages are by weight)

| 2.1 Emulsifiable concentrates | (a) | (b) | (c) |
|---|---|---|---|
| a compound of Tables 1 to 3 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2 Solutions | (a) | (b) | (c) | (d) |
|---|---|---|---|---|
| a compound of Tables 1 to 3 | 80% | 10% | 5% | 95% |
| ethylene glycol monomethyl ether | 20% | — | — | — |
| polyethylene glycol 400 (mol wt.) | — | 70% | — | — |
| N-methyl-2-pyrrolidone | — | 20% | — | — |
| epoxidised coconut oil | — | — | 1% | 5% |
| petroleum distillate (boiling range 160-190°) | — | — | 94% | — |

These solutions are suitable for application in the form of microdrops.

| 2.3 Granulates | (a) | (b) |
|---|---|---|
| a compound of Tables 1 to 3 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4 Dusts | (a) | (b) |
|---|---|---|
| a compound of Tables 1 to 3 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of formula I (throughout, percentages are by weight)

| 2.5 Wettable powders | (a) | (b) | (c) |
|---|---|---|---|
| a compound of Tables 1 to 3 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| 2.6 Emulsifiable concentrate | |
|---|---|
| a compound of Tables 1 to 3 | 10% |
| octylphenol polyethlene glycol ether (4-5 moles of ethylene oxide) | 3% |
| calcium dodecylbenzenesulfonate | 3% |
| castor oil polyglycol ether | 4% |

| -continued | |
|---|---|
| 2.6 Emulsifiable concentrate | |
| (36 moles of ethylene oxide) cyclohexanone | 30% |
| xylene mixture | 50% |

Emulsions of any required concentration can be obtained from this concentrate by dilution with water.

| 2.7 Dusts | (a) | (b) |
|---|---|---|
| a compound of Tables 1 to 3 | 5% | 8% |
| talcum | 95% | — |
| kaolin | — | 92% |

Ready-for-use dusts are obtained by mixing the active ingredient with the carriers, and grinding the mixture in a suitable mill.

| 2.8 Extruder granulate | |
|---|---|
| a compound of Tables 1 to 3 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a strem of air.

| 2.9 Coated granulate | |
|---|---|
| a compound of Tables 1 to 3 | 3% |
| polyethylene glycol 200 (mol wt.) | 3% |
| kaolin | 94% |

The finely ground active ingredient is uniformly applied, in a mixer, to the kaolin moistened with polyethylene glycol. Non-dusty coated granulates are obtained in this manner.

| 2.10 Suspension concentrate | |
|---|---|
| a compound of Tables 1 to 3 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the aduvants, giving a suspension concentrate from which suspensions of any desired concentration can be obtained by dilution with water.

3. BIOLOGICAL EXAMPLES

EXAMPLE 3.1

Action against Puccinia graminis on wheat (a) Residual-protective action

Wheat plants were treated 6 days after sowing with a spray mixture prepared from a wettable powder formulation of the active ingredient (0.02%). After 24 hours the treated plants were infected with a uredospore suspension of the fungus. The infected plants were incubated for 48 hours at 95–100% relative humidity and about 20° C. and then stood in a greenhouse at about 22° C. Evaluation of rust pustule development was made 12 days after infection.

(b) Systemic action

Wheat plants were treated 5 days after sowing with a spray mixture prepared from a wettable powder formulation of the test compound (0.006% based on the volume of the soil). After 48 hours the treated plants were infected with a uredospore suspension of the fungus. The plants were then incubated for 48 hours at 95–100% relative humidity and about 20° C. and then stood in a greenhouse at about 22° C. Evaluation or rust pustule development was made 12 days after infection.

Compounds of the tables were very effective against Puccinia fungi. Puccinia attack on untreated and infected control plants was 50–100%. For example compounds 1.2; 1.3; 1.6; 1.8; 1.9; 1.12; 1.13; 1.15; 1.16; 1.19; 1.27; 1.52; 1.55; 1.59; 1.68; 1.69; 1.72; 1.81; 1.90; 1.118; 1.120; 1.122; 1.124; 1.125; 1.126; 1.127; 1.129; 1.131; 1.133; 1.134 und 2.2; 2.11; 2.14; 2.28; 2.39; 3.3; 3.4; 3.7; 3.14 inhibited Puccinia attack almost completely (0–10%).

EXAMPLE 3.2

Action against Cercospora arachidicola in groundnut plants

Residual protective action

Groundnut plants 10–15 cm in height were sprayed with a spray mixture (0.02%) prepared from a wettable powder formulation of the test compound, and infected 48 hours later with a conidia suspension of the fungus. The infected plants were incubated for 72 hours at about 21° C. and high humidity and then stood in a greenhouse until the typical leaf specks occurred. Evaluation of the fungicidal action was made 12 days after infection and was based on the number and size of the specks.

Compared with untreated and infected controls (number and size of the specks=100%), Cercospora attack on groundnut plants treated with compounds of the tables was substantially reduced. In the above test, compounds 1.1; 1.2; 1.3; 1.4; 1.6; 1.7; 1.9; 1.12; 1.13; 1.15; 1.16; 1.19; 1.21; 1.23; 1.27; 1.52; 1.55; 1.59; 1.68; 1.69; 1.72; 1.77; 1.81; 1.90; 1.116; 1.118; 1.119; 1.120; 1.121; 1.122; 1.123; 1.124; 1.125; 1.127; 1.128; 1.129; 1.131; 1.133; 1.134; 2.2; 2.11; 2.14; 2.30; 2.39 and 3.3; 3.7 inhibited the occurrence of specks almost completely (0–10%).

EXAMPLE 3.3

Action against Erysiphe graminis on barley (a) Residual protective action

Barley plants about 8 cm in height were sprayed with a spray mixture (0.02%) prepared from a wettable powder formulation of the test compound. The treated plants were dusted with conidia of the fungus after 3–4 hours. The infected barley plants were then stood in a greenhouse at about 22° C. The extent of the infestation was evaluated after 10 days.

(b) Systemic action

Barley plants about 8 cm in height were treated with a spray mixture (0.006%), based on the volume of the soil) prepared from a wettable powder formulation of compound. Care was taken that the spray mixture did not come in contact with the growing parts of the plants. The treated plants were infected 48 hours later with a conidia suspension of the fungus. The infected barley plants were then stood in a greenhouse at about 22° C. and evaluation of infestation was made after 10 days.

Compounds of Tables 1 to 3 were very effective against Erysiphe fungi. Erysiphe attack was 100% on untreated and infected control plants. Compounds 1.1; 1.2; 1.3; 1.4; 1.6; 1.7; 1.8; 1.9; 1.12; 1.13; 1.15; 1.16; 1.19; 1.21; 1.23; 1.27; 1.52; 1.55; 1.59; 1.60; 1.68; 1.69; 1.72; 1.77; 1.81; 1.90; 1.118; 1.119; 1.120; 1.122; 1.123; 1.124; 1.125; 1.126; 1.127; 1.128; 1.129; 1.131; 1.133; 1.134; 2.2; 2.11; 2.14; 2.28; 2.39 and 3.2; 3.3; 3.7; 3.14 inhibited fungus attack on barley to 0–5%.

EXAMPLE 3.4

Residual-protective action against Venturia inaequalis on apple shoots

Apple cuttings with 10–20 cm long fresh shoots were sprayed with a spray mixture (0.02%) prepared from a wettable powder formulation of the test compound. The plants were infected 24 hours later with a conidia suspension of the fungus. The plants were then incubated for 5 days at 90–100% relative humidity and stood in a greenhouse for a further 10 days at 20°–24° C. Scab infestation was evaluated 15 days after infection. Compounds of the tables inhibited attack to less than 10%. On the other hand, Venturia attack on untreated and infected control shoots was 100%. Compounds 1.1; 1.2; 1.3; 1.4; 1.6; 1.7; 1.9; 1.12; 1.15 und 1.16; 1.19; 1.21; 1.68; 1.77; 1.81; 1.90; 1.118; 1.122; 1.123; 2.2; 2.11; 2.39 and 3.3 inhibited fungus attack on apple shoots to 0–5%.

EXAMPLE 3.5

Action against Botrytis cinerea on apples Residual protective action

Artifically damaged apples were treated by dropping a spray mixture (0.02%) prepared from the respective test compound formulated as wettable powder onto the injury sites. The treated fruit was then inoculated with a spore suspension of *Botrytis cinerea* and incubated for 1 week at high humidity and about 20° C. Evaluation was made by counting the number of injury sites attacked by rot and deducing the fungicidal action of the test compound therefrom. Compounds 1.4, 1.12, 1.15, 1.16, 1.19, 1.27, 1.68, 1.77, 1.81 and 1.90 inhibited fungus attack to 0–5%.

EXAMPLE 3.6

Action against Pyricularia oryzae on rice plants (a) Residual protective action

After a cultivation period of 2 weeks, rice plants were sprayed with a spray mixture (0.02%) prepared from a wettable powder formulation of the test compound. After 48 hours the treated plants were infected with a conidia suspension of the fungus. Evaluation of fungus attack was made after incubation for 5 days at 95–100% relative humidity and 24° C.

(b) Systemic action

A spray mixture (0.006%, based on the volume of the soil) prepared from a wettable powder formulation of the test compound was poured onto 2-week-old rice plants growing in conventional flower pots. The pots were then filled with water until the lowermost parts of the rice stalks are standing in water. After 48 hours the treated rice plants were infected with a conidia suspension of the fungus. Fungus attack was evaluated after the infected plants had been incubated for 5 days at 95–100% relative humidity and c. 24° C.

Compounds of Tables 1–3 were very effective against the Pyricularia fungus, whereas Pyricularia attack was 100% on untreated and infected control plants. Thus e.g. compounds 1.3; 1.15; 1.52; 1.90 and 1.119 inhibited fungus attack to 0–5%.

EXAMPLE 3.7

Action against Tilletia caries on wheat

Seeds of winter wheat of the Probus variety which were artificially infected with smut spores of Tilletia caries (3 g of dry spore material per 1 kg of seeds) were dressed on a mixer roll with the test fungicide at a concentration of 60 ppm of test compound (based on the weight of the seeds). The infected and treated wheat was sown in October in the open with a seeder in plots 2 meters long and in 3 rows. Three replicates were carried out with each test compound at its given concentration. To determine the effectiveness of the test compounds, the percentage of ears attacked by Tilletia was assessed at the time of ear ripening.

Compounds of Tables 1 to 3 were very effective against Tilletia. Tilletia attack was 100% on untreated and infected control plants. Thus e.g. compounds 1.3; 1.16; 2.2 and 3.14 inhibited fungus attack to 0–5%.

EXAMPLE 3.8

Action against Helminthosporium gramineum on barley

Seeds of winter barley of the "C1" variety which were naturally infected with Helminthosporium gramineum were dressed on a mixer roll with the test fungicide at concentrations of 60 ppm of test compound (based on the weight of the seeds). The infected and treated barley was sown in October in the open with a seeder in plots 2 meters long and in 3 rows. Three replicates were carried out with each test compound at its given concentration. Until evaluation was made, the test plants were cultivated under normal field conditions. To determine the effectiveness of the test compounds, the percentage of stalks attacked by Helminthosporium was assessed at the time of ear emergence.

Compounds of Tables 1 to 3 were very effective against Helminthosporium, whereas fungus attack was 100% on untreated and infected control plants. Thus e.g. compounds 1.3 and 1.6 inhibited fungus attack to 0–5%.

The closest structurally related compounds of the prior art were tested in comparison with the compounds of the present invention by means of the biological tests described above.

Prior art compounds of formula

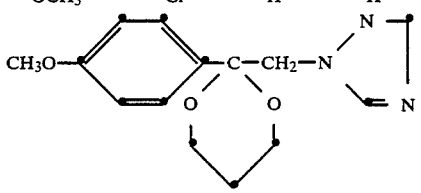

| Comp. | $R_a$ | $R_b$ | $R_c$ | $R_d$ | Publication |
|---|---|---|---|---|---|
| A | H | H | H | H | US 4 160 838; Comp. 2/Tab. I |
| B | H | $OCH_3$ | H | H | US 4 160 838; Example XIV |
| C | H | $OCH_3$ | H | $CH_3$ | US 4 160 838; Example XX/5 |
| D | Cl | $OCH_3$ | H | H | US 4 160 838; Comp. 31/Tab. I |
| E | $OCH_3$ | H | H | H | US 4 160 838; Comp. 17/Tab. I |
| F | $OCH_3$ | Cl | H | H | US 4 160 838; Example XXXIII/6 |
| G | | | | | US 4 160 838; Example XXI/5 |

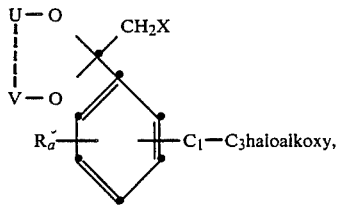

Biological Tests (Residual activity)

1. Evaluation scale

| Rating | Percentage activity | Fungus attack |
|---|---|---|
| 1 | $\geq 95$ | 0–5% |
| 3 | 80–95 | 5–20% |
| 6 | 50–80 | 20–50% |
| 9 | $\leq 50$ | $\geq 50\%$ |

A compound is regarded as ineffective if the fungus attack on the plant is 50% or greater.

2. Test results

| Comp. | Puccinia 200/20 ppm | | Cerospora 200/20 ppm | | Erysiphe 200/20 ppm | | Venturia 200/20 ppm | |
|---|---|---|---|---|---|---|---|---|
| A | 9 | 9 | 9 | 9 | 9 | 9 | 9 | 9 |
| B | 9 | 9 | 9 | 9 | 9 | 9 | 9 | 9 |
| C | 3 | 9 | 9 | 9 | 6 | 9 | 9 | 9 |
| D | 1 | 9 | 9 | 9 | 1 | 6 | 6 | 9 |
| E | 9 | 9 | 9 | 9 | 1 | 6 | 5 | 9 |
| F | 6 | 9 | 9 | 9 | 1 | 1 | 9 | 9 |
| G | 5 | 9 | 6 | 9 | 1 | 9 | 9 | 9 |
| 1.2 | 1 | 1 | 1 | 1 | 1 | 1 | 1 | 6 |
| 1.3 | 1 | 1 | 1 | 1 | 1 | 1 | 1 | 3 |
| 1.4 | 1 | 3 | 1 | 3 | 1 | 1 | 1 | 3 |
| 1.6 | 1 | 1 | 1 | 1 | 1 | 6 | 1 | 1 |
| 1.8 | 1 | 1 | 3 | 3 | 1 | 1 | 9 | 9 |
| 1.9 | 1 | 1 | 1 | 5 | 1 | 1 | 1 | 1 |
| 1.12 | 1 | 1 | 1 | 1 | 1 | 1 | 1 | 1 |
| 1.13 | 1 | 1 | 1 | 1 | 1 | 1 | 1 | 3 |
| 1.15 | 1 | 1 | 1 | 1 | 1 | 1 | 1 | 1 |
| 1.16 | 1 | 1 | 1 | 1 | 1 | 1 | 1 | 1 |
| 2.2 | 1 | 1 | 3 | 3 | 1 | 1 | 3 | 9 |
| 2.39 | 1 | 1 | 3 | 3 | 1 | 1 | 3 | 9 |
| 3.3 | 1 | 3 | 1 | 3 | 1 | 1 | 1 | 3 |

What is claimed is:

1. A compound of formula III

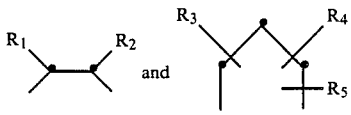

wherein one of the two phenyl substituents is in 2-position and the other is in 4-position, and wherein $R_a$ is halogen, methyl or $C_1$-$C_3$haloalkoxy, U and V both taken together are an alkylene bridge selected from $R_1$, $R_2$ and $R_3$, $R_4$, $R_5$ $R_1$ and $R_2$ are each independently of the other hydrogen, $C_1$-$C_6$alkyl, $C_1$-$C_6$alkyl which is substituted by one or more halogen atoms, or are phenyl or phenyl which is substituted by one or more halogen atoms and/or $C_1$-$C_2$alkyl groups or are the group —$CH_2$—Z—$R_6$; or $R_1$ and $R_2$ together form a tetramethylene bridge which is unsubstituted or substituted by $C_1$-$C_4$alkyl; and Z is an oxygen or sulfur atom, $R_6$ is hydrogen, $C_1$-$C_6$alkyl or $C_1$-$C_6$alkyl which is substituted by one or more halogen atoms or $C_1$-$C_3$alkoxy groups, or is $C_3$-$C_4$alkenyl, 2-propynyl (=propargyl), 3-halo-2-propynyl, phenyl or benzyl, each unsubstituted or substituted in the aromatic ring by one or more of halogen, $C_1$-$C_3$alkyl, $C_1$-$C_3$alkoxy, nitro and $CF_3$;

$R_3$, $R_4$ and $R_5$ are each independently hydrogen or $C_1$-$C_4$alkyl, with the proviso that the total number of carbon atoms in $R_3$, $R_4$ and $R_5$ may not exceed 6; and wherein X is halogen, benzenesulfonyloxy, p-tosloxy, trifluoroacetyloxy or lower alkylsulfonyloxy.

* * * * *